(12) United States Patent
Asagiri et al.

(10) Patent No.: US 8,912,499 B2
(45) Date of Patent: Dec. 16, 2014

(54) RADIOACTIVE RAY DETECTING APPARATUS, METHOD OF MANUFACTURING THE SAME, AND IMAGING SYSTEM

(75) Inventors: Satoru Asagiri, Yokohama (JP); Takayuki Yamazaki, Otawara (JP); Michito Nakayama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 617 days.

(21) Appl. No.: 13/045,770

(22) Filed: Mar. 11, 2011

(65) Prior Publication Data
US 2011/0226957 A1 Sep. 22, 2011

(30) Foreign Application Priority Data
Mar. 16, 2010 (JP) ................ P2010-059151

(51) Int. Cl.
*G01T 1/20* (2006.01)
*G01T 1/29* (2006.01)

(52) U.S. Cl.
CPC .................. *G01T 1/2985* (2013.01)
USPC ............. 250/370.11; 250/370.14; 250/390.02

(58) Field of Classification Search
CPC ................ G01T 1/2018; G01T 1/208
USPC ............ 250/370.11, 370.14, 390.02
See application file for complete search history.

(56) References Cited

U.S. PATENT DOCUMENTS

| | | | |
|---|---|---|---|
| 6,618,938 B1 * | 9/2003 | Alagaratnam et al. | 29/840 |
| 6,933,489 B2 * | 8/2005 | Fujii et al. | 250/214.1 |
| 7,103,398 B2 * | 9/2006 | Sieburg | 600/393 |
| 7,233,061 B1 * | 6/2007 | Conn | 257/686 |
| 7,245,022 B2 * | 7/2007 | Farooq et al. | 257/778 |

(Continued)

FOREIGN PATENT DOCUMENTS

| | | |
|---|---|---|
| CN | 1636278 A | 7/2005 |
| CN | 1732377 A | 2/2006 |

(Continued)

OTHER PUBLICATIONS

Extended European Search Report issued Jun. 4, 2013, in European Patent Application No. 11156945.5.

(Continued)

*Primary Examiner* — David Porta
*Assistant Examiner* — Djura Malevic
(74) *Attorney, Agent, or Firm* — Oblon, Spivak, McClelland, Maier & Neustadt, L.L.P.

(57) ABSTRACT

According to one embodiment, a radioactive ray detecting apparatus includes: a scintillator that produces visible light from a radioactive ray; a light detecting portion including a light receiving element that generates an electrical signal on a basis of intensity of visible light; a first board; a first electrical connection unit that electrically connects the light detecting portion and a first surface of the first board to each other; a second board disposed to face the first board; a second electrical connection that electrically connects a first surface of the second board and a second surface of the first board being opposite from the first surface of the first board to each other; and a data acquisition device that processes an electrical signal transmitted from the light detecting portion through the first electrical connection unit, the first board, the second electrical connection unit, and the second board.

7 Claims, 9 Drawing Sheets

(56) References Cited

U.S. PATENT DOCUMENTS

| | | | |
|---|---|---|---|
| 7,566,960 B1 * | 7/2009 | Conn | 257/686 |
| 7,606,346 B2 * | 10/2009 | Tkaczyk et al. | 378/19 |
| 2001/0040272 A1 * | 11/2001 | Mashino | 257/532 |
| 2002/0036340 A1 * | 3/2002 | Matsuo et al. | 257/698 |
| 2002/0038851 A1 * | 4/2002 | Kajiwara et al. | 250/368 |
| 2002/0041489 A1 * | 4/2002 | Fritz | 361/767 |
| 2002/0085336 A1 * | 7/2002 | Winer et al. | 361/306.3 |
| 2002/0088977 A1 * | 7/2002 | Mori et al. | 257/68 |
| 2003/0122083 A1 * | 7/2003 | Possin et al. | 250/370.11 |
| 2003/0155516 A1 | 8/2003 | Spartiotis et al. | |
| 2003/0164548 A1 * | 9/2003 | Lee | 257/738 |
| 2004/0067605 A1 * | 4/2004 | Koizumi | 438/108 |
| 2004/0113086 A1 * | 6/2004 | Heismann et al. | 250/370.09 |
| 2004/0178348 A1 * | 9/2004 | Wainer et al. | 250/370.09 |
| 2004/0201367 A1 * | 10/2004 | Echigo et al. | 320/166 |
| 2004/0210122 A1 * | 10/2004 | Sieburg | 600/393 |
| 2005/0167603 A1 | 8/2005 | Hoffman | |
| 2005/0179128 A1 * | 8/2005 | Shioga et al. | 257/724 |
| 2005/0230630 A1 * | 10/2005 | Yanagita et al. | 250/370.09 |
| 2006/0197083 A1 | 9/2006 | Suzuki et al. | |

FOREIGN PATENT DOCUMENTS

| | | |
|---|---|---|
| CN | 101006362 A | 7/2007 |
| CN | 101278208 A | 10/2008 |
| EP | 1 603 155 A1 | 12/2005 |
| JP | 2001-215281 A | 8/2001 |
| JP | 2003-264280 A | 9/2003 |
| JP | 2007-97930 A | 4/2007 |
| JP | 2008-259733 | 10/2008 |
| WO | WO 2004/059268 A1 | 7/2004 |

OTHER PUBLICATIONS

T. Solf, et al., "Solid-State Detector Stack for ToF-PET/MR", 2009 IEEE Nuclear Science Symposium Conference Record, XP-031826278, Oct. 24, 2009, pp. 2798-2799.

Office Action issued Mar. 5, 2013, in Japanese Patent Application No. 2010-059151 with English translation.

Chinese Office Action issued Dec. 5, 2012, in China Patent Application No. 201110054853.X (with English translation).

Chinese Office Action issued Jun. 20, 2013, in China Patent Application No. 201110054853.X (with English translation).

* cited by examiner

RADIOACTIVE RAY DETECTING APPARATUS, METHOD OF MANUFACTURING THE SAME, AND IMAGING SYSTEM

CROSS REFERENCE TO RELATED APPLICATION

This application is based upon and claims the benefit of priority from Japanese Patent Application No. 2010-059151, filed on Mar. 16, 2010; the entire contents of which are incorporated herein by reference.

FIELD

Embodiments described herein relate generally to: a radioactive ray detecting apparatus used to take a tomographic image of a subject by irradiating the subject with a radioactive ray; a method of manufacturing a radioactive ray detecting apparatus; and an imaging system.

BACKGROUND

An imaging system is also termed as a diagnostic imaging system. An example of the imaging system is X-ray CT (Computed Tomography) systems which are used in medical institutions such as hospitals. A gantry of an X-ray CT system includes an X-ray detecting apparatus. An X-ray beam generated by an X-ray tube is projected on a subject in accordance with the rotation of this X-ray tube. The X-ray beam transmitted through the subject enters the X-ray detecting apparatus. Thus, a tomographic image of the subject is acquired.

The X-ray detecting apparatus converts the X-ray beam, which has entered the X-ray detecting apparatus, to visible light. This visible light is converted to an electrical signal by a photodiode array mounted on a wiring board. Subsequently, after amplified, this electrical signal is converted to a digital electrical signal by an analog/digital conversion device (A/D conversion device) of a data acquisition system (DAS). This digitized data signal is sent from the data acquisition system to a console by use of a data transmission system.

The X-ray detecting apparatus includes a detector. This detector is configured including multiple detector modules arranged two-dimensionally. A bed on which the subject lies is moved in a body axis direction of the subject, and is thus inserted into an opening in the gantry, which is disclosed in Japanese Patent Application Publication No. 2008-259733.

DETAILED DESCRIPTION

According to one embodiment, a radioactive ray detecting apparatus includes a scintillator, a light detecting portion, a first board, a first electrical connection unit, a second board, a second electrical connection unit, and a data acquisition device. The scintillator is configured to produce visible light by receiving a radioactive ray. The light detecting portion includes a light receiving element disposed on the scintillator. The light detecting portion is configured to generate an electrical signal on a basis of intensity of the visible light produced by the scintillator. The first electrical connection unit is configured to electrically connect the light detecting portion and a first surface of the first board to each other. The second board is disposed to face the first board. The second electrical connection unit is configured to electrically connect a first surface of the second board and a second surface of the first board being opposite from the first surface of the first board to each other. The data acquisition device is disposed on a second surface of the second board being opposite from the first surface of the second board. The data acquisition device is configured to process an electrical signal transmitted from the light detecting portion through the first electrical connection unit, the first board, the second electrical connection unit, and the second board.

Various embodiments will be described hereinafter with reference to the accompanying drawings.

Figure 1:
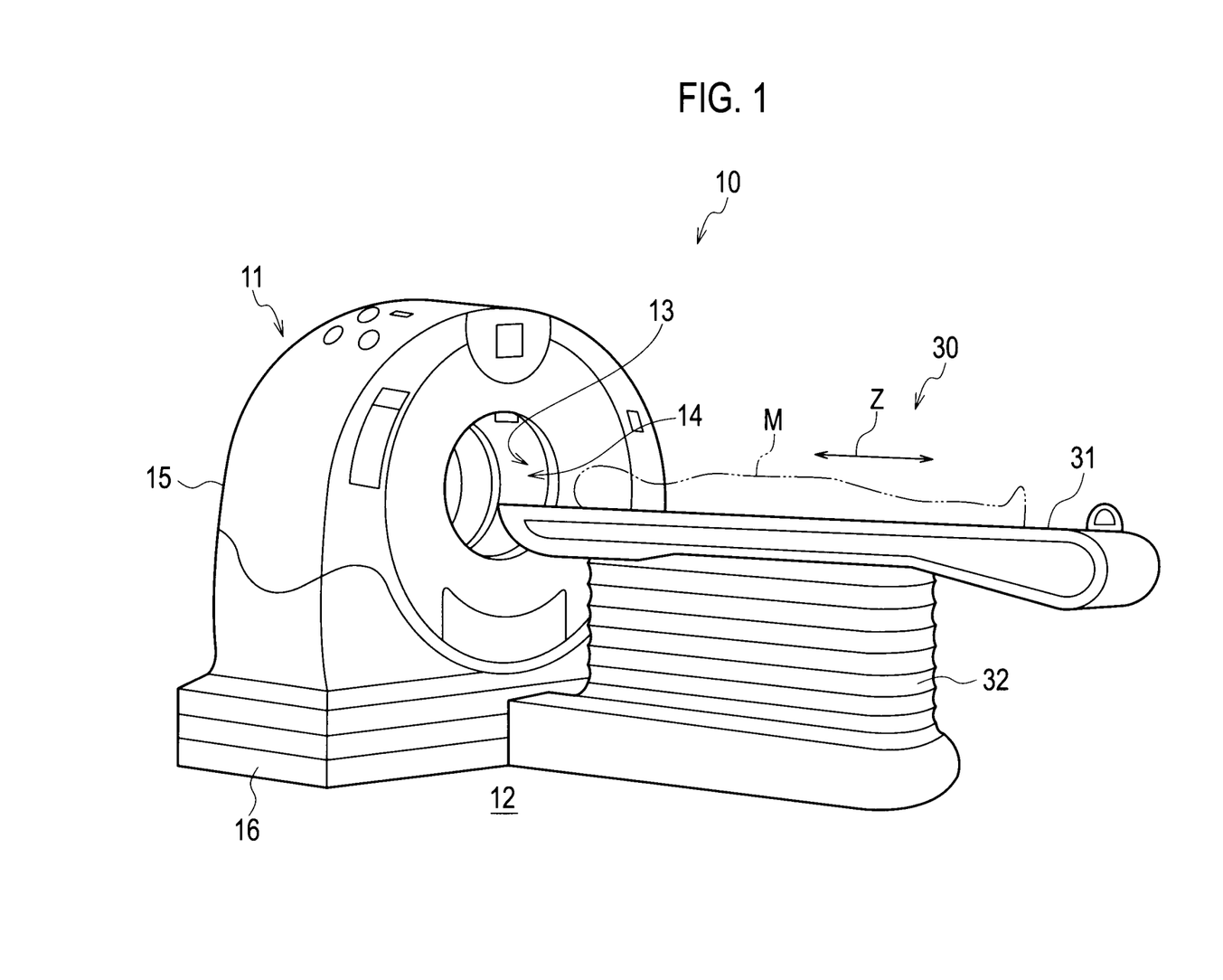
FIG. 1 is a perspective view showing an X-ray CT system configured to take a tomographic image for medical diagnosis, which is an example of an imaging system of an embodiment.
Figure 2:
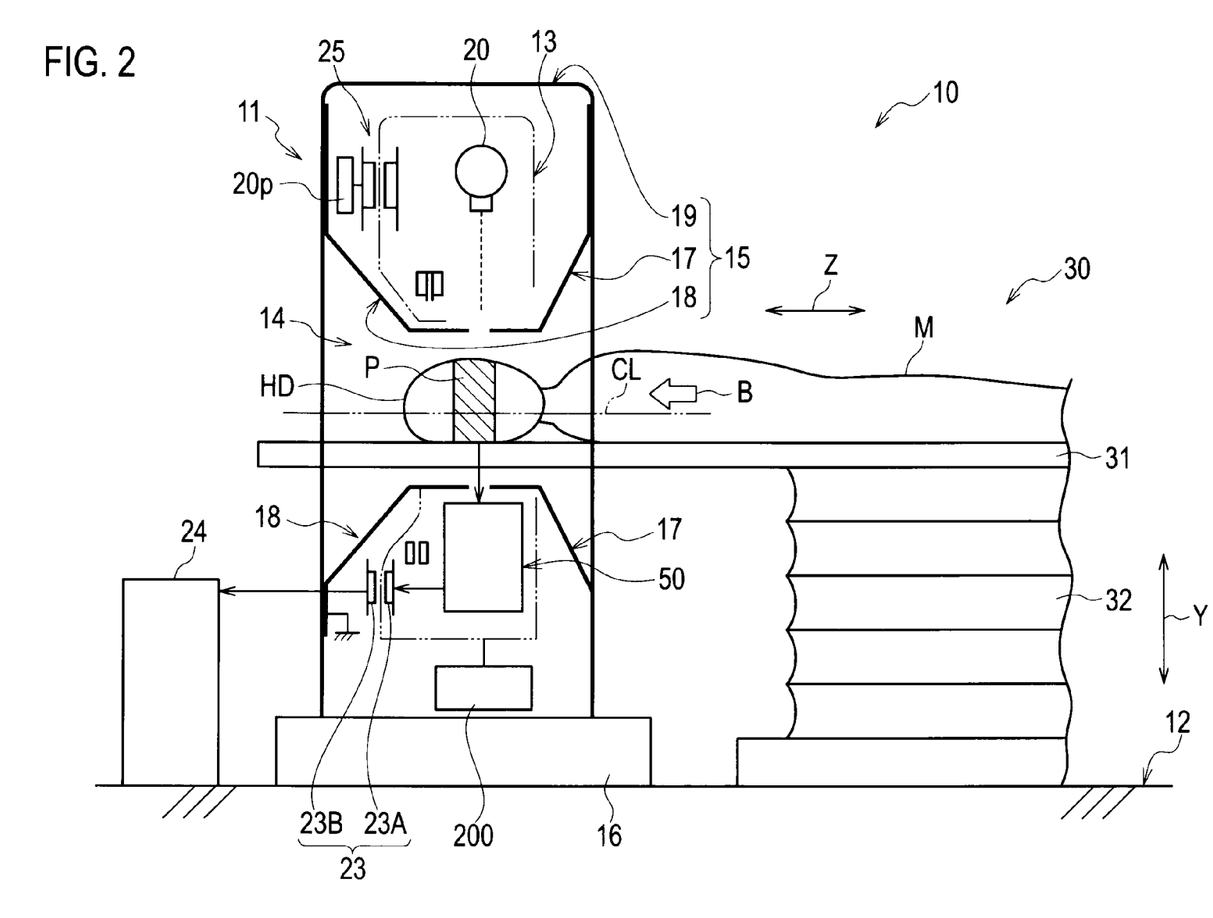
FIG. 2 is a diagram showing an example of an internal configuration of the X-ray CT system shown in FIG. 1.

FIG. 1 is a perspective view showing an X-ray CT (Computed Tomography) system configured to take a tomographic image for medical diagnosis, which is an example of an imaging system of an embodiment. FIG. 2 is a diagram showing an example of an internal configuration of the X-ray CT system shown in FIG. 1.

An X-ray CT system 10 shown in FIG. 1 includes a gantry 11 and a bed 30. The gantry 11 and the bed 30 are placed on a placement surface 12. A rotary unit 13 is provided inside the gantry 11. A circular opening 14 is provided in a place which is a center portion of the gantry 11 and concurrently a center portion of the rotary unit 13. For a medical examination and imaging, together with a top board 31 of the bed 30, a subject M laid on the top board 31 is inserted into the opening 14 by their movement in a Z direction (in an axial direction of the opening 14), and can be positioned depending on the necessity.

In this respect, referring to FIG. 2, detailed descriptions will be provided for a configuration example of the gantry 11.

As shown in FIG. 2, the gantry 11 includes a main body cover 15 and a base 16. The main body cover 15 is provided on the base 16. The base 16 is placed on the placement surface 12.

Descriptions will be provided for a structural example of the main body cover 15. As shown in FIG. 2, the main body cover 15 includes a front cover portion 17, a rear cover portion 18 and a top cover portion 19. The front cover portion 17, the rear cover portion 18 and the top cover portion 19 cover the rotary unit 13. The front cover portion 17 and the rear cover portion 18 form the opening 14.

As shown in FIG. 2, the rotary unit 13 includes: an X-ray tube 20 functioning as a source of generating an X-ray which is an example of radioactive rays; a radioactive ray detecting apparatus 50 configured to detect an X-ray beam from the X-ray tube 20; and a high voltage generator 202. The X-ray tube 20 and the radioactive ray detecting apparatus 50 are disposed opposed to each other with the center axis of the opening 14 as the center.

As illustrated in FIG. 2, for example, the head HD of the subject M laid on the top board 31 together with the top board 31 of the bed 30 is inserted into the opening 14. Subsequently, the X-ray tube 20 exposes, for example, the head of the subject M to an X-ray beam (X-ray beam projection). The X-ray beam transmitted through the head HD, for example, is detected by the radioactive ray detecting apparatus 50. Thereby, the radioactive ray detecting apparatus 50 temporarily converts the detected X-ray dose to visible light, and further converts this visible light to an analog electrical signal through photoelectric conversion. Subsequently, the radioactive ray detecting apparatus 50 converts the analog electrical signal to digital data (projection data) through an analog/digital conversion and amplification in each data acquisition system (DAS). Descriptions will be provided later for a structure of the radioactive ray detecting apparatus 50.

A data transmitter 23 shown in FIG. 2 is that through which the above-mentioned digital data is transmitted from the radioactive ray detecting apparatus 50 to a console 24 in a noncontact manner. The transmission of the digital data to the console 24 through the data transmitter 23 is achieved by sending the digital data from a transmitter 23A near the rotary unit 13 to a receiver 23B near a fixture of the gantry 11. Thereby, the console 24 is capable of acquiring a tomographic image of the subject M.

The rotary unit 13 is further provided with a slip ring 25. The slip ring 25 supplies a high voltage from the high voltage generator 20P to the X-ray tube 20.

The bed 30 shown in FIG. 2 includes the top board 31 and a base seat 32. The subject M is laid on the top board 31.

The base seat 32 is capable of positioning the top board 31 in a height direction by moving the top board 31 upward and downward in a Y direction, and is capable of positioning the top board 31 in the horizontal direction by moving the top board 31 in the Z direction. The Y direction and the Z direction are orthogonal to each other. The Z direction is parallel with a body axis CL of the subject M.

Figure 3:
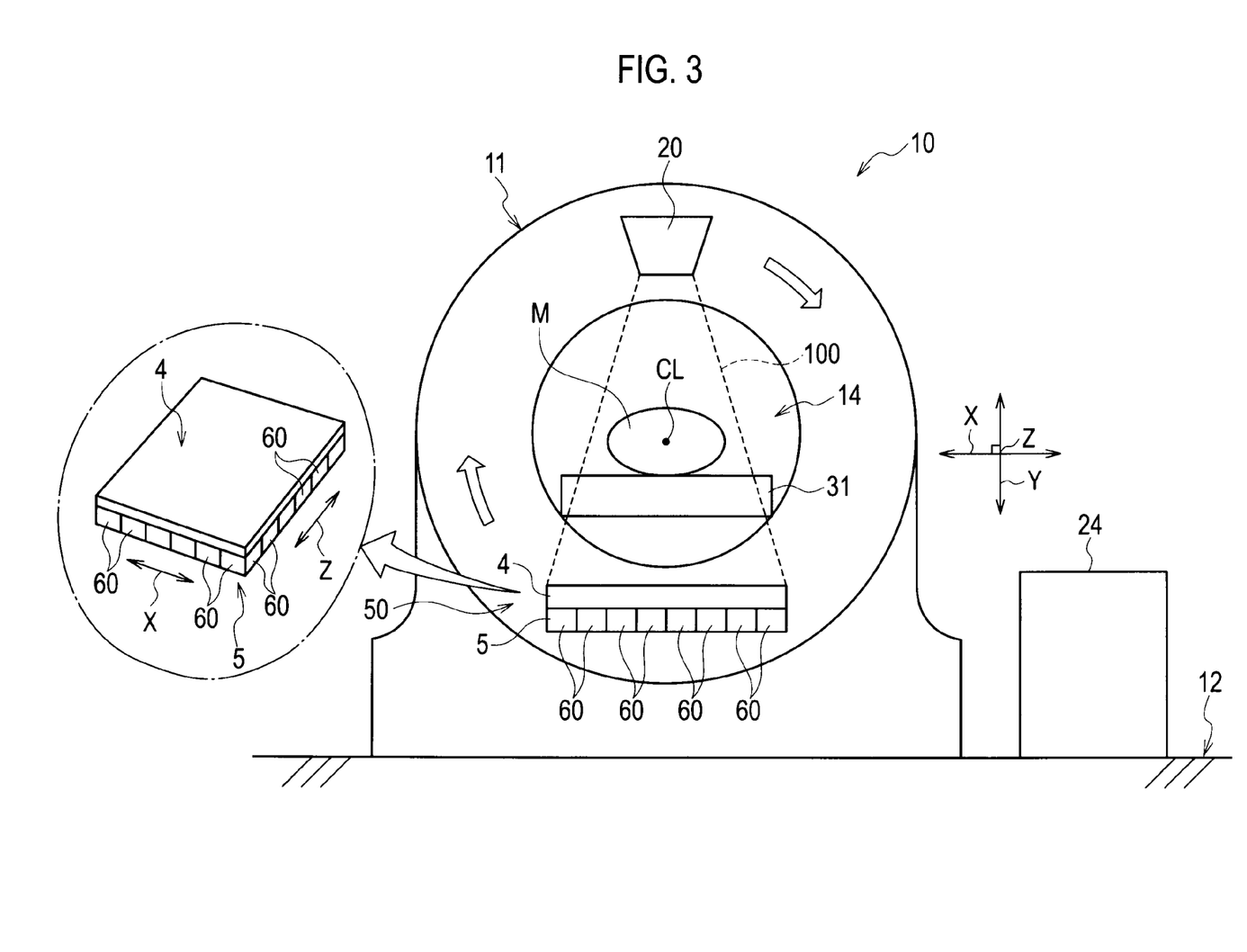
FIG. 3 is a front view of a gantry shown in FIG. 2, which is viewed in a B direction.

Next, FIG. 3 is a front view of the gantry 11 shown in FIG. 2, which is viewed in a B direction.

As shown in FIG. 3, the X-ray tube 20 and the radioactive ray detecting apparatus 50 are disposed opposed to each other with the opening 14 interposed in between. FIG. 3 shows a state in which the subject M and the top board 31 are positioned in the opening 14. A sector-shaped region indicated by broken lines shows an example of a projection range of an X-ray beam 100 which is an example of radioactive rays. This X-ray beam 100 is projected on the radioactive ray detecting apparatus 50. In FIG. 3, as an example, the radioactive ray detecting apparatus 50 is positioned in parallel with a plane which extends in the X direction and the Z direction. The rotary unit 13 shown in FIG. 2, which includes the X-ray tube 20 and the radioactive ray detecting apparatus 50, is configured to rotate around the opening 14 by operation of an actuator 200 shown in FIG. 2.

As shown in FIG. 3, the radioactive ray detecting apparatus 50 includes a collimator 4 and a detector 5 which are assembled in a stack. This detector 5 includes multiple detector modules 60. The detector modules 60 are arranged in a two-dimensional array in the X direction and the Z direction on the back of the collimator 4.

Figure 4:
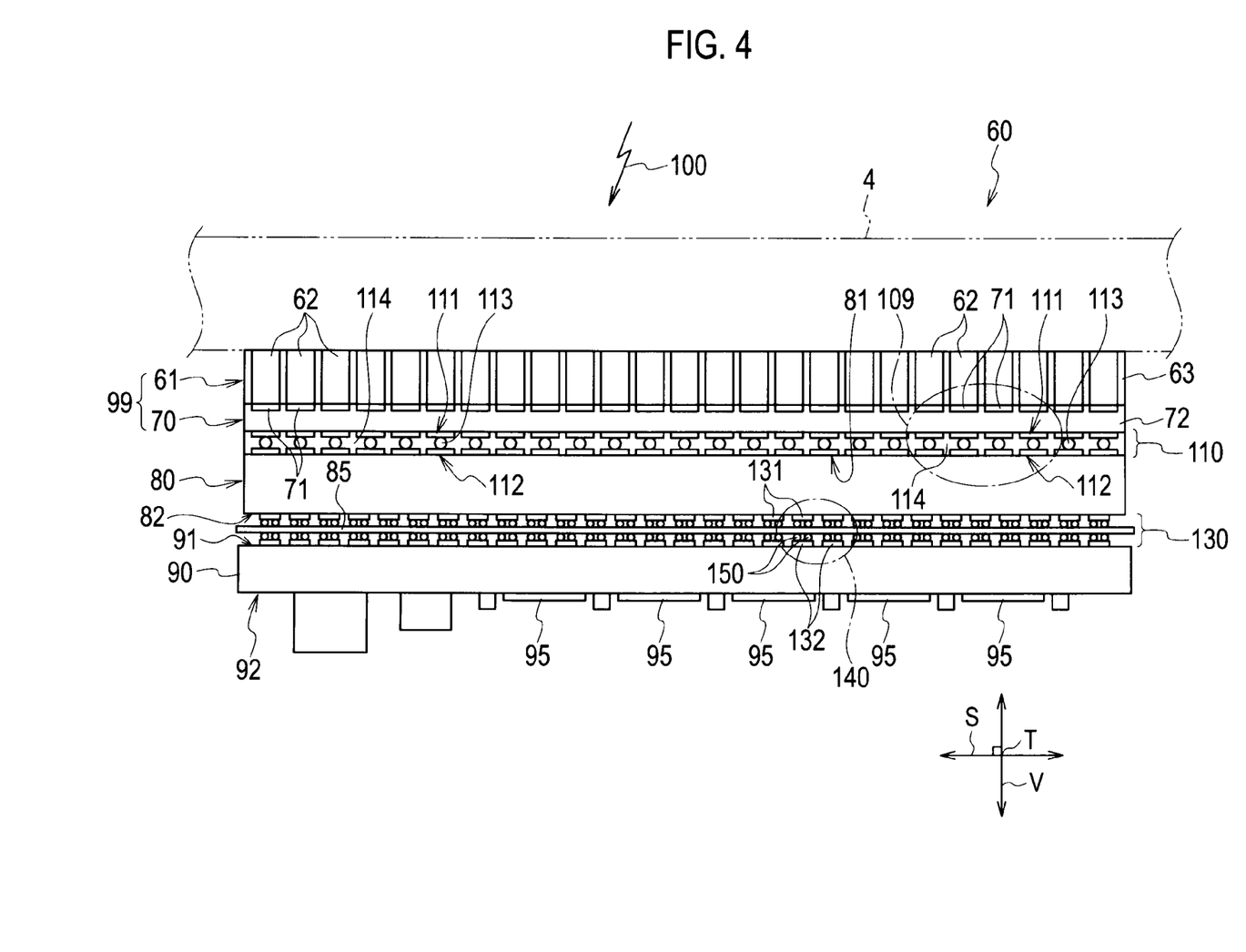
FIG. 4 is a diagram showing a preferable structural example of a detector module in a radioactive ray detecting apparatus.

FIG. 4 is a diagram showing a preferable structural example of the detector modules 60 in the detector 5.

Each detector module 60 shown in FIG. 4 includes: a plate-shaped scintillator unit 61 placed inside the collimator 4; a plate-shaped light detecting portion 70; a ceramic board 80 serving as a first board; a sheet connector 85; a printed wiring board 90 serving as a second board; and multiple data acquisition systems 95 which are smaller and thinner than the printed wiring board 90. In the detector module 60, the scintillator unit 61, the light detecting portion 70, the ceramic board 80, the sheet connector 85, the printed wiring board 90 and the data acquisition systems 95 are stacked one on another in a stacking direction V, and thus forms a block.

The collimator 4 shown in FIG. 3 is provided to effectively expose the scintillator unit 61 shown in FIG. 4 to the X-ray beam 100, which is generated by the X-ray tube 20, and removes noise which is attributable to the X-ray beam and the like reflected from other parts. The scintillator 61 includes a base material 63 and multiple scintillators 62. In the base material 63, the scintillators 62 are arranged in a two-dimensional array in an S direction and a T direction. The S direction and the T direction are orthogonal to each other, and are both orthogonal to the stacking direction V of the elements. Each scintillator 62 generates visible light by receiving the X-ray beam 100.

As shown in FIG. 4, the light detecting portion 70 includes a base material 72, and multiple photodiodes 71, each of which is an example of a light detecting element. On one surface of the base material 72, these photodiodes 71 are arranged in a two-dimensional array in the S direction and the T direction, and thus forms a photodiode array. The photodiodes 71 are disposed corresponding to the respective scintillators 62. The scintillator unit 61 and the light detecting portion 70 constitute a light-sensitive surface portion 99. Each photodiode 71 generates an electrical signal on the basis of the intensity of the visible light generated by the corresponding scintillator 62. Thereby, each scintillator 62 converts the X-ray beam 100 having traveled through the collimator 4 shown in FIG. 3 to visible light, and allows this visible light to reach the corresponding photodiode 71. Thus, the photodiode 71 is capable of converting the visible light to the electrical signal on the base of the intensity of the visible light.

Figure 5:
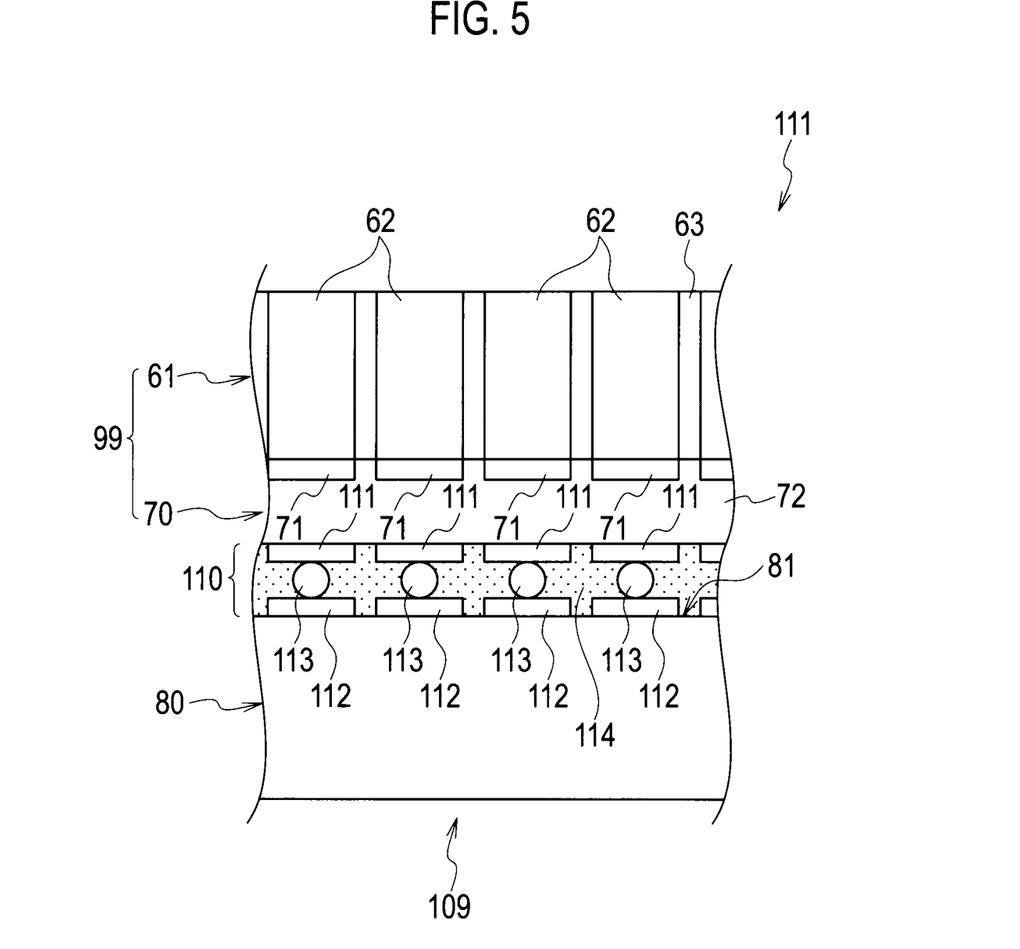
FIG. 5 is a magnified view showing part of a first electrical connection unit shown in FIG. 4.

As shown in FIG. 4, the light-sensitive surface portion 99 is mounted on the ceramic board 80. The light detecting portion 70 is electrically and mechanically connected to a first surface 81 of the ceramic board 80 with a first electrical connection unit 110 interposed in between. Referring to FIGS. 4 and 5, descriptions will be provided for the first electrical connection unit 110 between the light detecting portion 70 and the ceramic board 80. FIG. 5 shows, in a magnified manner, a part 109 of the first electrical connection unit 110 shown in FIG. 4.

As shown in FIGS. 4 and 5, the first electrical connection unit 110 has multiple bumps (an example of a protruding electrode) 113, as well as an electrically-conductive adhesive and an underfill 114, for the purpose of electrically and mechanically connecting electrical connection terminals 111 of the photodiodes 71 and electrical connection terminals 112 of the ceramic board 80, respectively.

The electrical connection terminals 111 of the photodiodes 71 are placed on the remaining surface of the base material 72. The bumps 113 are ball bumps. The bumps 113 electrically connect the electrical connection terminals 111 and the electrical connection terminals 112 of the ceramic board 80, respectively. The electrically-conductive adhesive and the underfill 114 fixes the remaining surface of the base material 72 and the first surface 81 of the ceramic board 80 together. Thereby, the light detecting portion 70 is fixedly attached to the first surface 81 of the ceramic board 80 by the underfill 114, inclusive of the electrically-conductive adhesive, with the multiple bumps 113 interposed in between.

Figure 6:
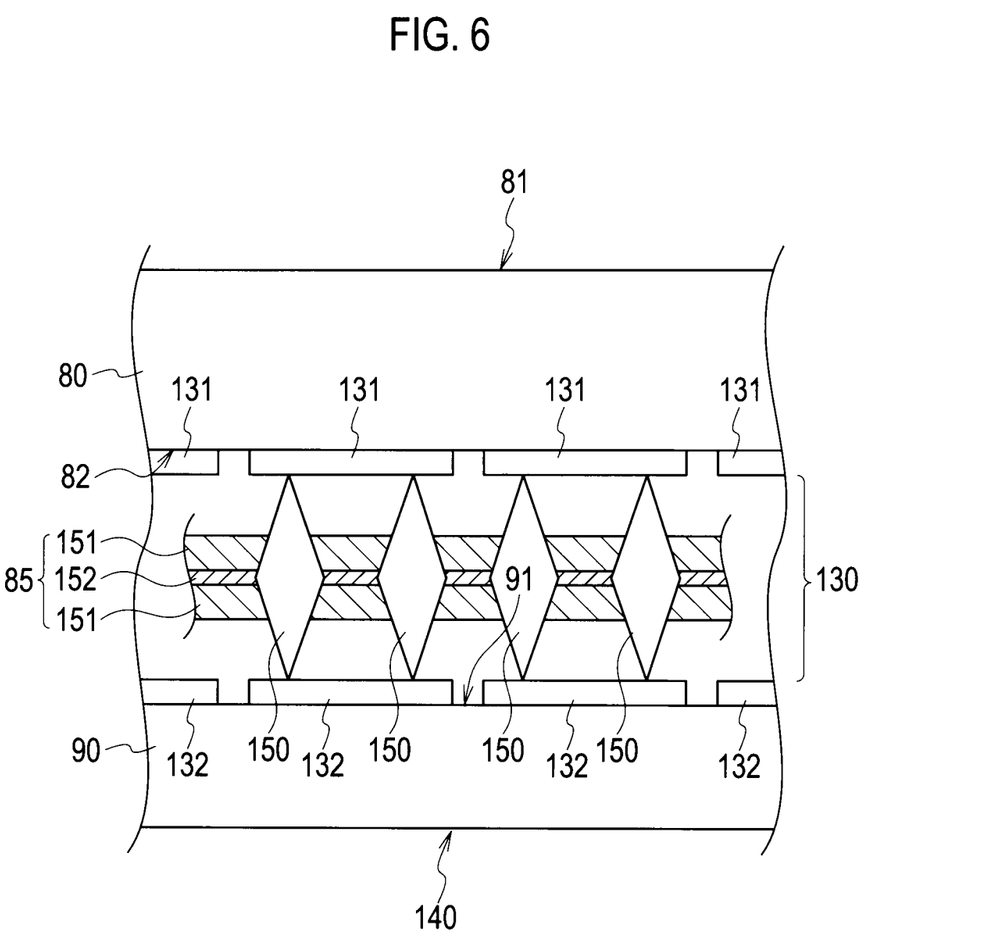
FIG. 6 is a magnified view showing part of a second electrical connection unit shown in FIG. 4.

Next, as shown in FIG. 4, a second surface 82 of the ceramic board 80 is electrically and mechanically connected to a first surface 91 of the printed wiring board 90 with a second electrical connection unit 130 interposed in between. Referring to FIGS. 4 and 6, descriptions will be provided for the second electrical connection unit 130 between the second surface 82 of the ceramic board 80 and the first surface 91 of the printed wiring board 90. FIG. 6 shows, in a magnified manner, a part 140 of the second electrical connection unit 130 shown in FIG. 4.

The second electrical connection unit 130 shown in FIGS. 4 and 6 has the sheet connector 85 for the purpose of electrically and mechanically connecting electrodes 131 of the second surface 82 of the ceramic board 80 and electrodes 132 of the first surface 91 of the printed wiring board 90, respectively. This sheet connector 85 includes multiple silver bumps (another example of the protrusion electrode) 150, two resin sheets (an example of an electrically-insulating sheet) 151, 151, and an adhesive sheet 152. The two resin sheets 151, 151 are bonded together by the adhesive sheet 152 while holding the silver bumps 150 at predetermined intervals. The silver bumps 150 electrically and mechanically connect the electrodes 131 of the second surface 82 of the ceramic board 80 and the electrodes 132 of the printed wiring board 90, respectively.

Various electronic parts, such as a connector 160 and a laser diode 161, and the multiple data acquisition systems 95 are mounted on the second surface 92 of the printed wiring board 90.

By this, each detector module 60 shown in FIG. 4 detects the X-ray beam 100 transmitted through the subject M, and converts the dose of the X-ray beam 100 transmitted through the subject M to the electrical signal. Each scintillator 62 generates fluorescent light upon reception of the X-ray beam 100. As the visible light, this fluorescent light is converted to the electrical signal (an electric current signal) by the corresponding photodiode 71. The electrical signal outputted from each photodiode 71 is guided to the second surface 82 of the ceramic board 80 through the first surface 81 of the ceramic board 80. The electrical signal outputted from each photodiode 71 is guided from the second surface 82 of the ceramic board 80 to the printed wiring board 90 through the silver bumps 150 of the sheet connector 85, and is subsequently sent to the data acquisition systems 95.

Once receiving the electrical signals outputted from the respective photodiodes 71, the data acquisition systems 95 performs a signal process. The processed signals are subjected to the analog-digital conversion by the A/D conversion devices in order that the computer can finally perform an arithmetic process on the signals. Thereafter, the resultant signals are sent to the computer in the console 24 shown in FIG. 1. Note that the number of data acquisition systems 95 to be placed on the printed wiring board 90 may be changed in accordance with the number of multi-slices depending on the necessity. In addition, it is desirable that the ceramic board 80, the printed wiring board 90 and the sheet connector 85 should be replaceable depending on the necessity by use of no specialized solvent. Even in a case where, for example, failure occurs in at least one of the ceramic board 80 and the printed wiring board 90, the configuration makes it possible to easily replace the board in which the failure occurs.

Each detector module 60 outputs the electrical signal which represents the intensity of the incident X-ray beam 100 and the attenuation of the X-ray beam 100 transmitted through the subject M. While the X-ray beam 100 is being scanned in order to acquire X-ray projection data, as shown in FIG. 3, the X-ray tube 20 and the radioactive ray detecting apparatus 50 rotate around the opening 14. An amplifying process, an A/D conversion process and the like are performed on X-ray transmission data which is sent to the data acquisition systems 95. Thereby, the X-ray projection data is acquired for each slice of the subject M.

As described above, the detector 5 is formed from the multiple detector modules 60 each having the above-described structure. Next, referring to FIGS. 7 to 9, descriptions will be provided for a method of manufacturing the detector module 60.

Figure 7:
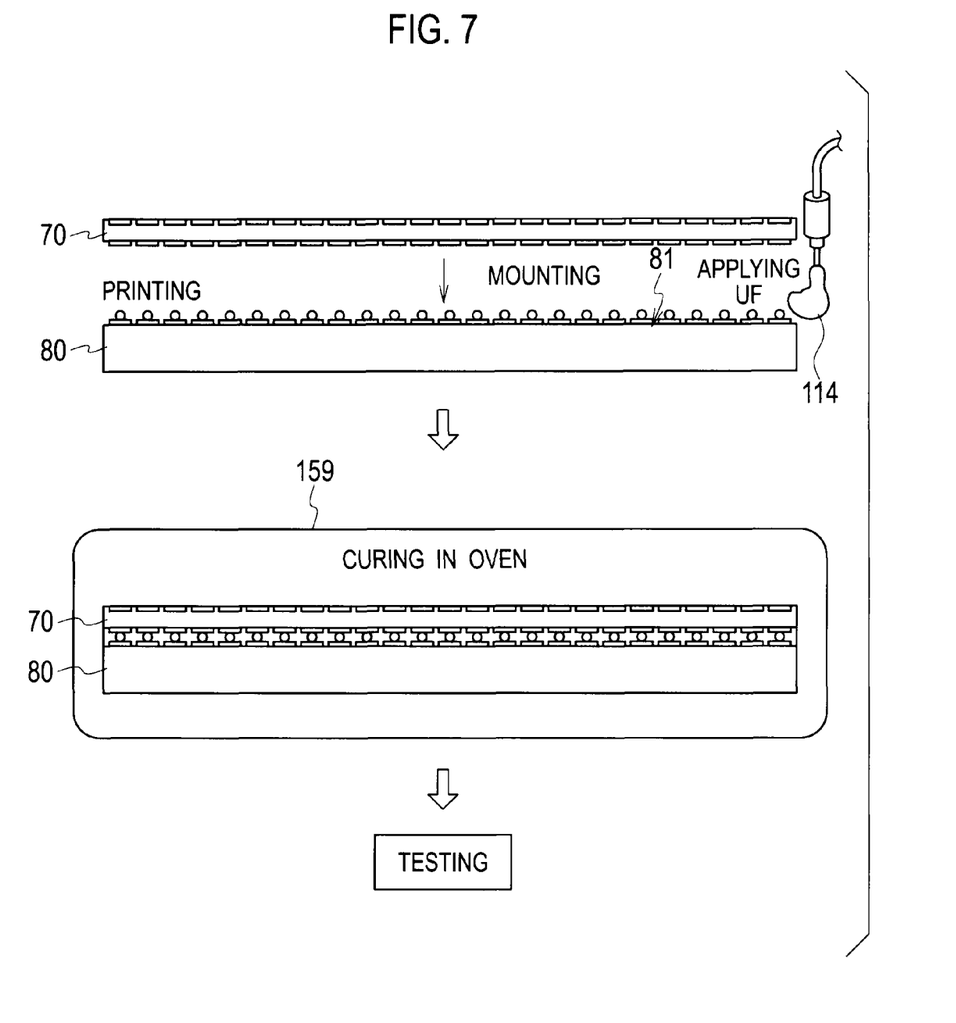
FIG. 7 is a diagram showing a light detecting portion fixing step of: mounting a light detecting portion on a first surface of a ceramic board; applying an underfill; and curing the underfill in an oven.

FIG. 7 shows a light detecting portion fixing step of: mounting the light detecting portion 70 on the first surface 81 of the ceramic board 80; applying the underfill 114; and curing the underfill 114 in an oven 159.

Figure 8:
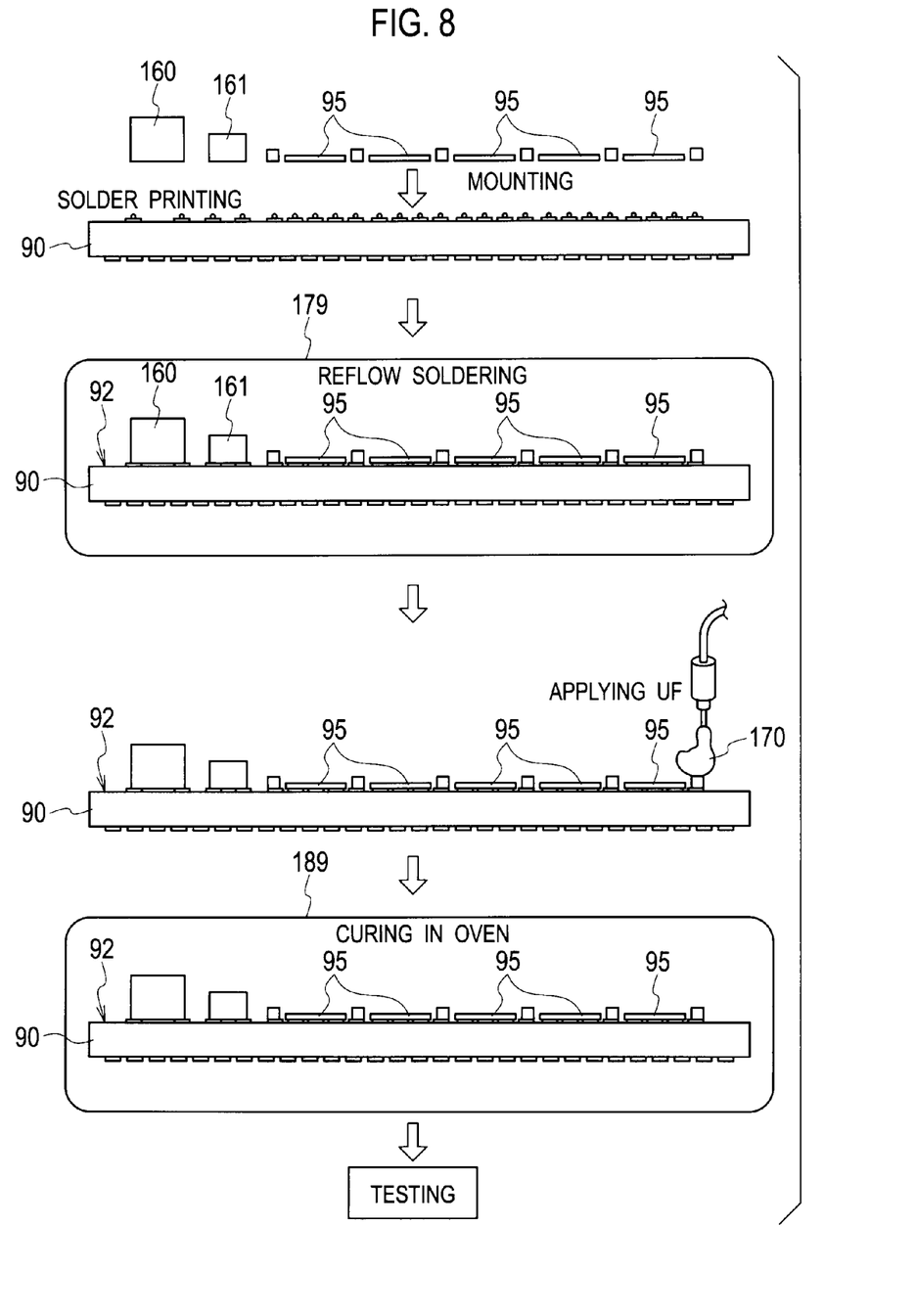
FIG. 8 is a diagram showing a data acquisition system arranging step of: mounting various electronic parts and multiple data acquisition systems on a second surface of a printed wiring board; performing soldering by use of reflow; thereafter applying an underfill; and curing the underfill in another oven.

FIG. 8 shows a data acquisition system arranging step of: mounting various electronic parts, such as the connector 160, and the multiple data acquisition systems 95 on the second surface 92 of the printed wiring board 90; performing soldering by use of a reflow 179; thereafter applying the underfill 170; and curing the underfill 170 in an oven 189.

Figure 9:
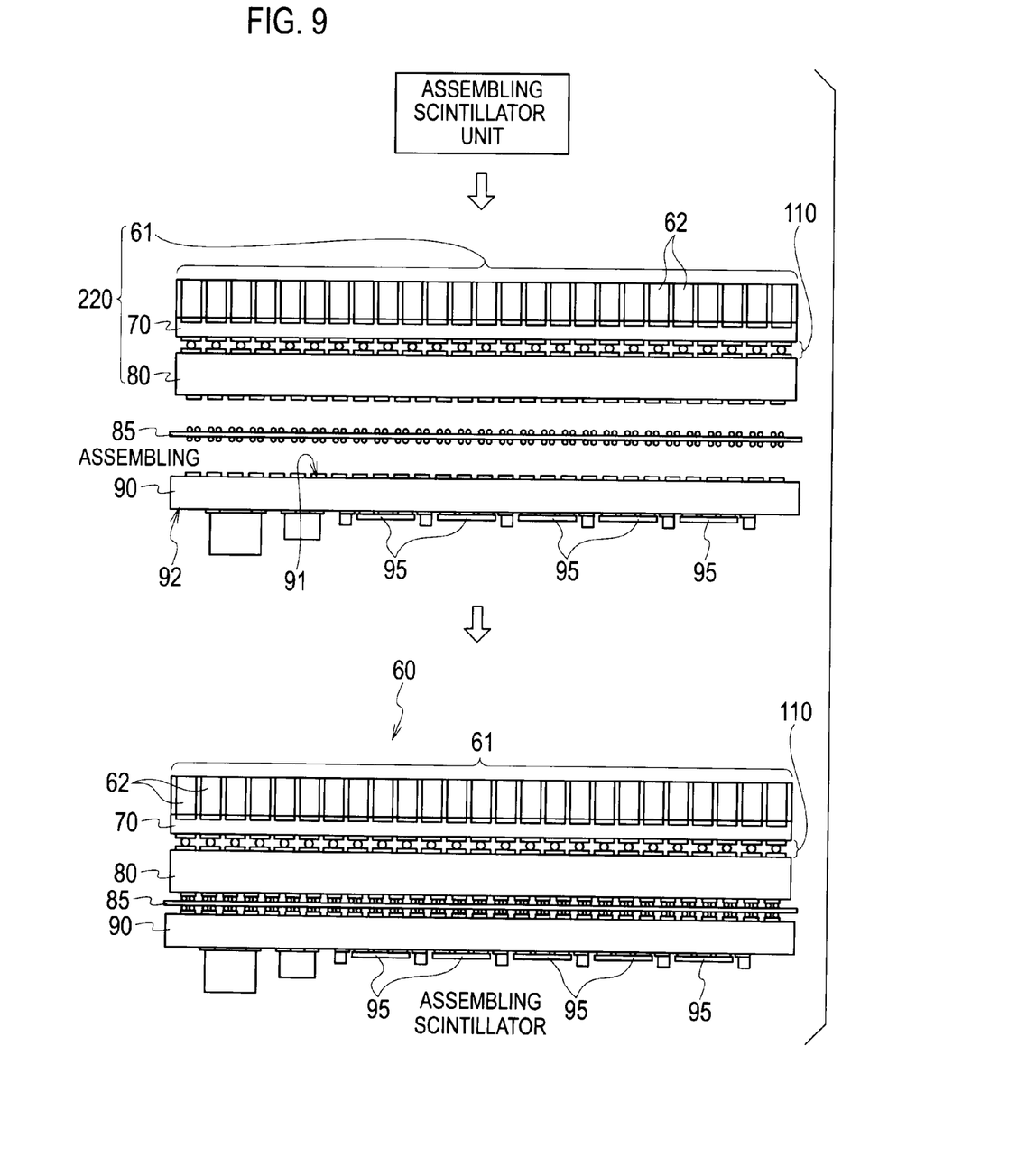
FIG. 9 is a diagram showing an assembling step of: assembling a scintillator unit with a unit obtained by assembling the ceramic board and the light detecting portion as shown in FIG. 7; and electrically connecting the printed board assembled as shown in FIG. 8 to the ceramic board by use of a sheet connector.

FIG. 9 shows an assembling step of: assembling the scintillator unit 61 with a unit obtained by assembling the ceramic board 80 and the light detecting portion 70 as shown in FIG. 7; and electrically and mechanically connecting the printed wiring board 90 assembled as shown in FIG. 8 to the ceramic board 80 by use of the sheet connector 85.

First of all, as shown in FIG. 7, an electrically-conductive paste serving as the electrically-conductive adhesive is printed on the first surface 81 of the ceramic board 80 serving as the first board, and the light detecting portion 70 is mounted on the first surface 81. Subsequently, the underfill 114 is applied to the first surface 81 and the light detecting portion 70. Thereafter, the unit formed from the ceramic board 80 and the light detection portion 70 is placed in the oven 159, and is heated, for example, for four hours at 150° C. Thus, the electrically-conductive paste and the underfill 114 are cured. After the curing, the unit formed from the ceramic board 80 and the light detecting portion 70 is sent to an inspection step, and is subjected to a predetermined test.

On the other hand, as shown in FIG. 8, solder is printed on the second surface 92 of the printed wiring board 90. Subsequently, for example, the connector 160, the laser diode 161 and the multiple data acquisition systems 95 are mounted and arranged on the printed wiring board 90. Thereafter, the printed wiring board 90 on which the multiple data acquisition systems 95 and the like are mounted is heated in the reflow 179, for example, at 250° C. for 10 minutes. Thus, the solder is connected by reflow. After that, the underfill 170 is applied to all the data acquisition systems 95. The resultant printed wiring board 90 is placed in the oven 189, and is heated, for example, at 100° C. for 30 minutes. Thereby, the underfill 170 is cured. After the curing, the printed wiring board 90 is sent to an inspection step, and is subjected to a predetermined test.

Finally, as shown in FIG. 9, the scintillator unit 61 is mounted on the light detecting portion 70. Thus, the scintillator unit 61 and the light detecting portion 70 are assembled together. Subsequently, a unit 220 including the ceramic board 80, the scintillator unit 61 and the light detecting portion 70 is electrically and mechanically connected to the printed wiring board 90 by use of the sheet connector 85. Thereby, the detector modules 60 for the detector 5 are completed.

As shown in FIG. 3, the detector modules 60 thus manufactured are two-dimensionally arrayed in the X direction and the Y direction. Thus, the flat-type detector 5 is constructed. Subsequently, this detector 5 and the collimator 4 are combined in a stack. Thereby, the radioactive ray detecting apparatus 50 is completed.

In the related X-ray CT system, the transmission of an analog signal from a detection module to a data acquisition system is achieved through flexible wiring members, such as a flexible board and a flexible cable, whose transmission distance is long. This makes the wiring length of the flexible wiring members longer, and the electrostatic capacitance of the wiring length of the flexible wiring members larger. Hence, the signal transmission is affected by the influence of minute vibrations from other parts and the electromagnetic field of the power supply system. Accordingly, the conversion of the analog signal to the digital signal by the data acquisition system is influenced by noise. As a countermeasure for this noise, for example, used is a shield structure in which ground wiring patterns are disposed on and under the signal wire. However, this shield structure still leaves the following problems unsolved: the wire capacitance remains large because the wiring length of the flexible wiring members is long; and the effect of the shield structure on the magnetic field is small.

By contrast to this, in the embodiment, as shown in FIG. 4, the light detecting portion 70 including the multiple photodiodes 71 is mounted on the first surface 81 of the ceramic board 80 by use of the first electrical connection unit 110. The multiple data acquisition system 95 is mounted on the second surface 92 of the printed wiring board 90. In addition, the second surface 82 of the ceramic board 80 is electrically and mechanically connected to the first surface 91 of the printed wiring board 90 with the sheet connector 85 of the second electrical connection unit 130. For this reason, the physical distances between the photodiodes 71 and the data acquisition systems 95 are extremely short, and the signal process for conversion from the analog signal to the digital signal by each data acquisition system 95 can be performed excellently because the signal conversion is hard to be affected by the bad effect of the noise. Thus, an image with higher quality can be obtained.

A radioactive ray detecting apparatus according to one embodiment includes: a scintillator configured to produce visible light by receiving a radioactive ray; a light detecting portion including a light receiving element disposed on the scintillator, and configured to generate an electrical signal on a basis of intensity of the visible light produced by the scintillator; a first board; a first electrical connection unit configured to electrically connect the light detecting portion and a first surface of the first board to each other; a second board disposed to face the first board; a second electrical connection unit configured to electrically connect a first surface of the second board and a second surface of the first board being opposite from the first surface of the first board to each other; and a data acquisition device disposed on a second surface of the second board being opposite from the first surface of the second board, and configured to process an electrical signal transmitted from the light detecting portion through the first electrical connection unit, the first board, the second electrical connection unit, and the second board.

The foregoing configuration reduces the noise induced by the analog signal while the detected analog signal is being transmitted to each data acquisition system, and accordingly makes it possible to provide a radioactive ray detecting apparatus which is capable of acquiring an image with a higher quality.

In a radioactive ray detecting apparatus according to one embodiment, the light detecting portion may include a first electrical connection terminal, the first surface of the first board may include a second electrical connection terminal, the first electrical connection unit may include a protruding electrode configured to electrically connect the first electrical connection terminal and the second electrical connection terminal, and the light detecting portion and the first surface of the first board may be fixed to each other by underfill.

The foregoing configuration enables the light detecting portion to be electrically connected and mechanically fixed to the first board by use of the first electrical connection unit.

In a radioactive ray detecting apparatus according to one embodiment, the second electrical connection unit may include: protruding electrodes; paired electrically-insulating sheets configured to hold the protruding electrodes; and an adhesive sheet configured to bond the paired electrically-insulating sheets to each other.

The foregoing configuration enables the second surface of the first board to be securely electrically connected to the first surface of the second board by use of the second electrical connection unit.

A method of manufacturing a radioactive ray detecting apparatus according to one embodiment includes: electrically connecting and fixing a light detecting portion to a first surface of a first board by use of a first electrical connection unit, the light detecting portion including a light receiving element configured to generate an electrical signal on a basis of intensity of visible light; disposing a data acquisition device on a second surface of a second board including a first surface and the second surface opposite from the first surface, the data acquisition device configured to process an electrical signal from the light detecting portion; and making assembly by disposing a scintillator on the light detecting portion, the scintillator configured to produce visible light by receiving a radioactive ray, and by electrically connecting the first surface of the second board and a second surface of the first board being opposite from the first surface of the first board so as to transmit an electrical signal from the light detecting portion to the data acquisition device through the first electrical connection unit, the first board, a second electrical connection unit, and the second board.

The foregoing configuration reduces the noise induced by the analog signal while the detected analog signal is being transmitted to each data acquisition system, and accordingly makes it possible to provide a radioactive ray detecting apparatus which is capable of acquiring an image with a higher quality.

An imaging system according to one embodiment includes: the radioactive ray detecting apparatus mentioned above; a radioactive ray generating source configured to radiate a radioactive ray to a subject; and a gantry configured to rotatably support the radioactive ray detecting apparatus and the radioactive ray generating source, and including an opening configured to allow the subject to be inserted between the radioactive ray detecting apparatus and the radioactive ray generating source, wherein an image of the subject is taken by driving the radioactive ray detecting apparatus to detect a radioactive ray radiated from the radioactive ray generating source and transmitted through the subject.

The foregoing configuration reduces the noise induced by the analog signal while the detected analog signal is being transmitted to each data acquisition system, and accordingly makes it possible to provide a radioactive ray detecting apparatus which is capable of acquiring an image with a higher quality.

While certain embodiments have been described, these embodiments have been presented by way of example only, are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In the illustrated case, for instance, the X-ray CT system is cited as an example of the imaging system, and the X-ray beam is used as an example of the radioactive ray. However, the imaging system is not limited to this. For instance, the imaging system of this embodiment is applicable as a PET (Positron Emission Computed Tomography). In the case of this PET, once the X-ray beam 100 from the X-ray tube 20 is projected onto the subject M and enters radiopharmaceuticals in the subject M, gamma rays occur from a bodily part in which the administered radiopharmaceuticals (tracer) stay, and the gamma rays fall on the scintillators. The scintillators convert the gamma rays to light, and the light is received by the light detecting portion.

As the concrete examples of the wired boards, the ceramic board and the printed board are used as the first board and the second board, respectively. However, no specific restriction is imposed on the first board or the second board. Arbitrary types of wiring board may be used as the first and second boards.

Furthermore, various embodiments can be carried out by combining the multiple configuration elements disclosed in the foregoing embodiment depending on the necessity. For instance, some configuration elements may be removed from all the configuration elements shown in the foregoing embodiment. Moreover, configuration elements related to a different embodiment may be combined depending on the necessity.

What is claimed is:

1. A radioactive ray detecting apparatus comprising:
a scintillator configured to produce visible light by receiving a radioactive ray;
a light detecting portion including a light receiving element disposed on the scintillator, and configured to generate an electrical signal on a basis of intensity of the visible light produced by the scintillator;
a first board made of ceramic;
a first electrical connection unit configured to electrically connect the light detecting portion and a first surface of the first board to each other;
a second board disposed to face the first board;
a second electrical connection unit configured to electrically connect a first surface of the second board and a second surface of the first board being opposite from the first surface of the first board to each other; and
a data acquisition device disposed on a second surface of the second board being opposite from the first surface of the second board, and configured to process an electrical signal transmitted from the light detecting portion through the first electrical connection unit, the first board, the second electrical connection unit, and the second board,
wherein the second electrical connection unit includes protruding electrodes,
paired electrically-insulating sheets configured to hold the protruding electrodes, and
a connector configured to connect the paired electrically-insulating sheets to each other.

2. The radioactive ray detecting apparatus according to claim 1, wherein
the light detecting portion includes a first electrical connection terminal,
the first surface of the first board includes a second electrical connection terminal,
the first electrical connection unit includes a protruding electrode configured to electrically connect the first electrical connection terminal and the second electrical connection terminal, and
the light detecting portion and the first surface of the first board are fixed to each other by underfill.

3. The radioactive ray detecting apparatus according to claim 1, wherein
the connector is an adhesive sheet configured to bond the paired electrically-insulating sheets to each other.

4. A method of manufacturing a radioactive ray detecting apparatus, the method comprising:
electrically connecting and fixing a light detecting portion to a first surface of a first board made of ceramic by use of a first electrical connection unit, the light detecting portion including a light receiving element configured to generate an electrical signal on a basis of intensity of visible light;
disposing a data acquisition device on a second surface of a second board including a first surface and the second surface opposite from the first surface, the data acquisition device configured to process an electrical signal from the light detecting portion; and
making assembly by disposing a scintillator on the light detecting portion, the scintillator configured to produce visible light by receiving a radioactive ray, and by electrically connecting the first surface of the second board and a second surface of the first board being opposite from the first surface of the first board so as to transmit an electrical signal from the light detecting portion to the data acquisition device through the first electrical connection unit, the first board, a second electrical connection unit, and the second board, the second electrical connection unit including protruding electrodes, paired electrically-insulating sheets configured to hold the protruding electrodes, and a connector configured to connect the paired electrically-insulating sheets to each other.

5. The method of manufacturing a radioactive ray detecting apparatus according to claim 4, wherein an adhesive sheet configured to bond the paired electrically-insulating sheets to each other is used as the connector.

6. An imaging system comprising:
a radioactive ray detecting apparatus including
a scintillator configured to produce visible light by receiving a radioactive ray,
a light detecting portion including a light receiving element disposed on the scintillator, and configured to generate an electrical signal on a basis of intensity of the visible light produced by the scintillator,
a first board made of ceramic, a first electrical connection unit configured to electrically connect the light detecting portion and a first surface of the first board to each other, a second board disposed to face the first board, a second electrical connection unit configured to electrically connect a first surface of the second board and a second surface of the first board being opposite from the first surface of the first board to each other, the second electrical connection unit including protruding electrodes, paired electrically-insulating sheets configured to hold the protruding electrodes, and a connector configured to connect the paired electrically-insulating sheet to each other, and a data acquisition device disposed on a second surface of the second board being opposite from the first surface of the second board, and configured to process an electrical signal transmitted from the light detecting portion through the first electrical connection unit, the first board, the second electrical connection unit, and the second board;

a radioactive ray generating source configured to radiate a radioactive ray to a subject; and a gantry configured to rotatably support the radioactive ray detecting apparatus and the radioactive ray generating source, and including an opening configured to allow the subject to be inserted between the radioactive ray detecting apparatus and the radioactive ray generating source, wherein an image of the subject is taken by driving the radioactive ray detecting apparatus to detect a radioactive ray radiated from the radioactive ray generating source and transmitted through the subject.

7. The imaging system according to claim 6, wherein the connector is an adhesive sheet configured to bond the paired electrically-insulating sheets to each other.

* * * * *